(12) United States Patent
Wood et al.

(10) Patent No.: US 7,371,319 B2
(45) Date of Patent: May 13, 2008

(54) PRODUCTION OF WATER FOR INJECTION USING REVERSE OSMOSIS

(75) Inventors: Jonathan Wood, Needham, MA (US); John Arba, Bradford, MA (US); Gary Zoccolante, Plymouth, MA (US); Anil Jha, Lincoln, MA (US)

(73) Assignee: Siemens Water Technologies Holding Corp., Warrendale, PA (US)

( * ) Notice: Subject to any disclaimer, the term of this patent is extended or adjusted under 35 U.S.C. 154(b) by 0 days.

(21) Appl. No.: 11/033,696

(22) Filed: Jan. 12, 2005

(65) Prior Publication Data

US 2005/0121388 A1    Jun. 9, 2005

Related U.S. Application Data

(63) Continuation of application No. 10/278,714, filed on Oct. 23, 2002.

(51) Int. Cl.
*B01D 61/16* (2006.01)
*B01D 65/00* (2006.01)

(52) U.S. Cl. .................. 210/85; 210/149; 210/195.2; 210/257.2; 210/181; 210/321.6

(58) Field of Classification Search ................ 210/85, 210/96.2, 143, 195.2, 257.2, 259, 321.69, 210/500.38, 181–184, 636, 637, 652, 774, 210/805, 806, 900, 149, 321.6
See application file for complete search history.

(56) References Cited

U.S. PATENT DOCUMENTS

| | | | |
|---|---|---|---|
| 2,514,415 A | 7/1950 | Rasch | |
| 2,681,319 A | 6/1954 | Bodamer | |
| 2,681,320 A | 6/1954 | Bodamer | |
| 2,788,319 A | 4/1957 | Pearson | |
| 2,794,777 A | 6/1957 | Pearson | |
| 2,815,320 A | 12/1957 | Kollsman | |
| 2,854,394 A | 9/1958 | Kollsman | |
| 2,923,674 A | 2/1960 | Kressman | |
| 2,943,989 A | 7/1960 | Kollsman | |
| 3,014,855 A | 12/1961 | Kressman | |
| 3,074,864 A | 1/1963 | Gaysowski | |
| 3,099,615 A | 7/1963 | Kollsman | |
| 3,148,687 A | 9/1964 | Dosch | |
| 3,149,061 A | 9/1964 | Parsi | |
| 3,149,062 A | 9/1964 | Gottschal et al. | |

(Continued)

FOREIGN PATENT DOCUMENTS

CA    2316012 A1    11/2001

(Continued)

OTHER PUBLICATIONS

U.S. Appl. No. 60/330,966, filed Nov. 5, 2001 by Smith for the US2003/0094406 document.*

(Continued)

*Primary Examiner*—Joseph Drodge

(57) ABSTRACT

A method and system for providing Water for Injection using reverse osmosis. Water for Injection can be produced by reverse osmosis and the reverse osmosis membrane can be kept in a constantly self-sanitizing condition. One way of obtaining a constantly self-sanitizing condition is to maintain the reverse osmosis membrane at an elevated temperature during production of Water for Injection.

7 Claims, 1 Drawing Sheet

U.S. PATENT DOCUMENTS

| | | | |
|---|---|---|---|
| 3,165,460 A | 1/1965 | Zang et al. | |
| 3,291,713 A | 12/1966 | Parsi | |
| 3,330,750 A | 7/1967 | McRae et al. | |
| 3,341,441 A | 9/1967 | Giuffrida et al. | |
| 3,375,208 A | 3/1968 | Duddy | |
| 3,627,703 A | 12/1971 | Kojima et al. | |
| 3,630,378 A | 12/1971 | Bauman | |
| 3,645,884 A | 2/1972 | Gilliland | |
| 3,686,089 A | 8/1972 | Korngold | |
| 3,755,135 A | 8/1973 | Johnson | |
| 3,869,375 A | 3/1975 | Ono et al. | |
| 3,869,376 A | 3/1975 | Tejeda | |
| 3,870,033 A | 3/1975 | Faylor et al. | |
| 3,876,565 A | 4/1975 | Takashima et al. | |
| 3,989,615 A | 11/1976 | Kiga et al. | |
| 4,032,452 A | 6/1977 | Davis | |
| 4,033,850 A | 7/1977 | Kedem et al. | |
| 4,089,758 A | 5/1978 | McAloon | |
| 4,116,889 A | 9/1978 | Chlanda et al. | |
| 4,119,581 A | 10/1978 | Rembaum et al. | |
| 4,130,473 A | 12/1978 | Eddleman | |
| 4,153,761 A | 5/1979 | Marsh | |
| 4,167,551 A | 9/1979 | Tamura et al. | |
| 4,191,811 A | 3/1980 | Hodgdon | |
| 4,197,206 A | 4/1980 | Karn | |
| 4,216,073 A | 8/1980 | Goldstein | |
| 4,217,200 A | 8/1980 | Kedem et al. | |
| 4,226,688 A | 10/1980 | Kedem et al. | |
| 4,228,000 A | 10/1980 | Hoeschler | |
| 4,294,933 A | 10/1981 | Kihara et al. | |
| 4,298,442 A | 11/1981 | Giuffrida | |
| 4,321,145 A | 3/1982 | Carlson | |
| 4,330,654 A | 5/1982 | Ezzell et al. | |
| 4,342,651 A | 8/1982 | Ahrens | |
| 4,358,545 A | 11/1982 | Ezzell et al. | |
| 4,374,232 A | 2/1983 | Davis | |
| 4,430,226 A | 2/1984 | Hedge et al. | |
| 4,465,573 A | 8/1984 | O'Hare | |
| 4,473,450 A | 9/1984 | Nayak et al. | |
| 4,505,797 A | 3/1985 | Hodgdon et al. | |
| 4,574,049 A | 3/1986 | Pittner | |
| 4,610,790 A * | 9/1986 | Reti et al. | 210/636 |
| 4,614,576 A | 9/1986 | Goldstein | |
| 4,632,745 A | 12/1986 | Giuffrida et al. | |
| 4,636,296 A | 1/1987 | Kunz | |
| 4,655,909 A | 4/1987 | Furuno et al. | |
| 4,661,411 A | 4/1987 | Martin et al. | |
| 4,671,863 A | 6/1987 | Tejeda | |
| 4,687,561 A | 8/1987 | Kunz | |
| 4,702,810 A | 10/1987 | Kunz | |
| 4,707,240 A | 11/1987 | Parsi et al. | |
| 4,747,929 A | 5/1988 | Siu et al. | |
| 4,747,955 A | 5/1988 | Kunin | |
| 4,751,153 A | 6/1988 | Roth | |
| 4,753,681 A | 6/1988 | Giuffrida et al. | |
| 4,770,793 A | 9/1988 | Treffry-Goatley et al. | |
| 4,804,451 A | 2/1989 | Palmer | |
| 4,804,474 A * | 2/1989 | Blum | 210/641 |
| 4,849,102 A | 7/1989 | Latour et al. | |
| 4,871,431 A | 10/1989 | Parsi | |
| 4,872,958 A | 10/1989 | Suzuki et al. | |
| 4,915,803 A | 4/1990 | Morris | |
| 4,925,541 A | 5/1990 | Giuffrida et al. | |
| 4,931,160 A | 6/1990 | Giuffrida | |
| 4,956,071 A | 9/1990 | Giuffrida et al. | |
| 4,964,970 A | 10/1990 | O'Hare | |
| 4,969,983 A | 11/1990 | Parsi | |
| 4,983,267 A | 1/1991 | Moeglich et al. | |
| 5,026,465 A | 6/1991 | Katz et al. | |
| 5,030,672 A | 7/1991 | Hann et al. | |
| 5,032,265 A * | 7/1991 | Jha et al. | 210/195.2 |
| 5,066,375 A | 11/1991 | Parsi et al. | |
| 5,066,402 A | 11/1991 | Anselme et al. | |
| 5,073,268 A | 12/1991 | Saito et al. | |
| 5,082,472 A | 1/1992 | Mallouk et al. | |
| 5,084,148 A | 1/1992 | Kazcur et al. | |
| 5,092,970 A | 3/1992 | Kaczur et al. | |
| 5,106,465 A | 4/1992 | Kaczur et al. | |
| 5,116,509 A | 5/1992 | White | |
| 5,120,416 A | 6/1992 | Parsi et al. | |
| 5,126,026 A | 6/1992 | Chlanda | |
| 5,128,043 A | 7/1992 | Wildermuth | |
| 5,154,809 A | 10/1992 | Oren et al. | |
| 5,166,220 A | 11/1992 | McMahon | |
| 5,176,828 A | 1/1993 | Proulx | |
| 5,196,115 A | 3/1993 | Andelman | |
| 5,203,976 A | 4/1993 | Parsi et al. | |
| 5,211,823 A | 5/1993 | Giuffrida et al. | |
| 5,223,103 A | 6/1993 | Kazcur et al. | |
| 5,240,579 A | 8/1993 | Kedem | |
| 5,254,227 A | 10/1993 | Cawlfield et al. | |
| 5,259,936 A | 11/1993 | Ganzi | |
| 5,292,422 A | 3/1994 | Liang et al. | |
| 5,308,466 A | 5/1994 | Ganzi et al. | |
| 5,308,467 A | 5/1994 | Sugo et al. | |
| 5,316,637 A | 5/1994 | Ganzi et al. | |
| 5,342,521 A | 8/1994 | Bardot et al. | |
| 5,346,624 A | 9/1994 | Libutti et al. | |
| 5,346,924 A | 9/1994 | Giuffrida | |
| 5,352,364 A * | 10/1994 | Kruger et al. | 210/652 |
| 5,356,849 A | 10/1994 | Matviya et al. | |
| 5,358,640 A | 10/1994 | Zeiher et al. | |
| 5,376,253 A | 12/1994 | Rychen et al. | |
| 5,401,421 A * | 3/1995 | Blum | 210/742 |
| 5,411,641 A | 5/1995 | Trainham, III et al. | |
| 5,425,858 A | 6/1995 | Farmer | |
| 5,425,866 A | 6/1995 | Sugo et al. | |
| 5,434,020 A | 7/1995 | Cooper | |
| 5,444,031 A | 8/1995 | Hayden | |
| 5,451,309 A | 9/1995 | Bell | |
| 5,458,787 A | 10/1995 | Rosin et al. | |
| 5,460,725 A | 10/1995 | Stringfield | |
| 5,460,728 A | 10/1995 | Klomp et al. | |
| 5,489,370 A | 2/1996 | Lomasney et al. | |
| 5,503,729 A | 4/1996 | Elyanow et al. | |
| 5,518,626 A | 5/1996 | Birbara et al. | |
| 5,518,627 A | 5/1996 | Tomoi et al. | |
| 5,536,387 A | 7/1996 | Hill et al. | |
| 5,538,611 A | 7/1996 | Otowa | |
| 5,538,655 A | 7/1996 | Fauteux et al. | |
| 5,539,002 A | 7/1996 | Watanabe | |
| 5,547,551 A | 8/1996 | Bahar et al. | |
| 5,558,753 A | 9/1996 | Gallagher et al. | |
| 5,580,437 A | 12/1996 | Trainham, III et al. | |
| 5,584,981 A | 12/1996 | Turner et al. | |
| 5,593,563 A | 1/1997 | Denoncourt et al. | |
| 5,599,614 A | 2/1997 | Bahar et al. | |
| 5,670,053 A | 9/1997 | Collentro et al. | |
| 5,679,228 A | 10/1997 | Elyanow et al. | |
| 5,679,229 A | 10/1997 | Goldstein et al. | |
| 5,681,438 A | 10/1997 | Proulx | |
| 5,714,521 A | 2/1998 | Kedem et al. | |
| 5,716,531 A | 2/1998 | Kenley et al. | |
| RE35,741 E | 3/1998 | Oren et al. | |
| 5,733,602 A | 3/1998 | Hirose et al. | |
| 5,736,023 A | 4/1998 | Gallagher et al. | |
| 5,759,373 A | 6/1998 | Terada et al. | |
| 5,762,421 A * | 6/1998 | Ross | 383/111 |
| 5,762,774 A | 6/1998 | Tessier | |
| 5,766,479 A | 6/1998 | Collentro et al. | |
| 5,804,055 A | 9/1998 | Coin et al. | |
| 5,814,197 A | 9/1998 | Batchelder et al. | |
| 5,837,124 A | 11/1998 | Su et al. | |
| 5,858,191 A | 1/1999 | DiMascio et al. | |

| | | |
|---|---|---|
| 5,868,915 A | 2/1999 | Ganzi et al. |
| 5,891,328 A | 4/1999 | Goldstein |
| 5,925,240 A | 7/1999 | Wilkins et al. |
| 5,928,807 A | 7/1999 | Elias |
| 5,954,935 A | 9/1999 | Neumeister et al. |
| 5,961,805 A | 10/1999 | Terada et al. |
| 5,980,716 A | 11/1999 | Horinouchi et al. |
| 6,056,878 A | 5/2000 | Tessier et al. |
| 6,074,551 A | 6/2000 | Jones et al. |
| 6,099,716 A | 8/2000 | Molter et al. |
| 6,103,125 A | 8/2000 | Kuepper |
| 6,126,834 A | 10/2000 | Tonelli et al. |
| RE36,972 E | 11/2000 | Baker et al. |
| 6,146,524 A | 11/2000 | Story |
| 6,149,788 A | 11/2000 | Tessier et al. |
| 6,171,374 B1 | 1/2001 | Barton et al. |
| 6,187,154 B1 | 2/2001 | Yamaguchi et al. |
| 6,187,162 B1 | 2/2001 | Mir |
| 6,190,528 B1 | 2/2001 | Li et al. |
| 6,190,553 B1 | 2/2001 | Lee |
| 6,190,558 B1 | 2/2001 | Robbins |
| 6,193,869 B1 | 2/2001 | Towe et al. |
| 6,197,174 B1 | 3/2001 | Barber et al. |
| 6,197,189 B1 | 3/2001 | Schwartz et al. |
| 6,214,204 B1 | 4/2001 | Gadkaree et al. |
| 6,228,240 B1 | 5/2001 | Terada et al. |
| 6,235,166 B1 | 5/2001 | Towe et al. |
| 6,248,226 B1 | 6/2001 | Shinmei et al. |
| 6,254,741 B1 | 7/2001 | Stuart et al. |
| 6,258,278 B1 | 7/2001 | Tonelli et al. |
| 6,267,891 B1 | 7/2001 | Tonelli et al. |
| 6,274,019 B1 | 8/2001 | Kuwata |
| 6,279,019 B1 | 8/2001 | Oh et al. |
| 6,284,124 B1 | 9/2001 | DiMascio et al. |
| 6,284,399 B1 | 9/2001 | Oko et al. |
| 6,296,751 B1 | 10/2001 | Mir |
| 6,303,037 B1 | 10/2001 | Tamura et al. |
| 6,342,163 B1 | 1/2002 | DeLong et al. |
| 6,365,023 B1 | 4/2002 | De Los Reyes et al. |
| 6,375,812 B1 | 4/2002 | Leonida |
| 6,391,178 B1 | 5/2002 | Garcia et al. |
| 6,402,916 B1 | 6/2002 | Sampson et al. |
| 6,402,917 B1 | 6/2002 | Emery et al. |
| 6,461,512 B1 | 10/2002 | Hirayama et al. |
| 6,468,430 B1 * | 10/2002 | Kimura et al. .............. 210/636 |
| 6,471,853 B1 * | 10/2002 | Moscaritolo ................. 210/85 |
| 6,471,867 B2 | 10/2002 | Sugaya et al. |
| 6,482,304 B1 | 11/2002 | Emery et al. |
| 6,485,649 B1 | 11/2002 | Terava et al. |
| 6,607,647 B2 | 8/2003 | Wilkins et al. |
| 6,607,668 B2 | 8/2003 | Rela |
| 6,627,073 B2 | 9/2003 | Hirota et al. |
| 6,648,307 B2 | 11/2003 | Nelson et al. |
| 6,649,037 B2 | 11/2003 | Liang et al. |
| 6,730,227 B2 | 5/2004 | Zeiher et al. |
| 6,766,812 B1 | 7/2004 | Gadini |
| 6,773,588 B2 * | 8/2004 | Beeman et al. ............. 210/232 |
| 6,783,666 B2 | 8/2004 | Takeda et al. |
| 6,808,608 B2 | 10/2004 | Srinivasan et al. |
| 6,824,662 B2 | 11/2004 | Liang et al. |
| 2001/0003329 A1 | 6/2001 | Sugaya et al. |
| 2002/0092769 A1 | 7/2002 | Garcia et al. |
| 2002/0139676 A1 | 10/2002 | Moulin et al. |
| 2002/0144954 A1 | 10/2002 | Arba et al. |
| 2003/0080467 A1 | 5/2003 | Andrews et al. |
| 2003/0089609 A1 | 5/2003 | Liang et al. |
| 2003/0094406 A1 * | 5/2003 | Smith ....................... 210/96.2 |
| 2003/0098266 A1 | 5/2003 | Shiue et al. |
| 2003/0155243 A1 | 8/2003 | Sferrazza |
| 2003/0201235 A1 | 10/2003 | Chidambaran et al. |
| 2004/0079700 A1 | 4/2004 | Wood et al. |
| 2005/0016932 A1 | 1/2005 | Arba et al. |
| 2005/0103622 A1 | 5/2005 | Jha et al. |
| 2005/0103631 A1 | 5/2005 | Freydina et al. |
| 2005/0103644 A1 | 5/2005 | Wilkins et al. |
| 2005/0103722 A1 | 5/2005 | Freydina et al. |
| 2005/0103723 A1 | 5/2005 | Wilkins et al. |
| 2005/0109703 A1 | 5/2005 | Newenhizen |
| 2006/0060532 A1 | 3/2006 | Davis |

FOREIGN PATENT DOCUMENTS

| | | |
|---|---|---|
| CN | 1044411 A | 8/1990 |
| DE | 1 201 055 | 9/1965 |
| DE | 3238280 A1 | 4/1984 |
| DE | 4016000 C2 | 11/1991 |
| DE | 44 18 812 A1 | 12/1995 |
| DE | 199 42 347 A1 | 3/2001 |
| EP | 0170895 B1 | 2/1986 |
| EP | 0 462 606 A1 | 12/1991 |
| EP | 0 503 589 A1 | 9/1992 |
| EP | 0 621 072 A2 | 10/1994 |
| EP | 0 680 932 A2 | 11/1995 |
| EP | 0803474 A2 | 10/1997 |
| EP | 0 870 533 A1 | 10/1998 |
| EP | 1 068 901 A2 | 1/2001 |
| EP | 1068901 A2 | 1/2001 |
| EP | 1075 868 A2 | 2/2001 |
| EP | 1 101 790 A1 | 5/2001 |
| EP | 1 106 241 A1 | 6/2001 |
| EP | 1172145 A2 | 1/2002 |
| EP | 1222954 A1 | 7/2002 |
| EP | 1506941 A1 | 2/2005 |
| GB | 776469 | 6/1957 |
| GB | 877239 | 9/1961 |
| GB | 880344 | 10/1961 |
| GB | 893051 | 4/1962 |
| GB | 942762 | 11/1963 |
| GB | 1048026 | 11/1966 |
| GB | 1137679 | 12/1968 |
| GB | 1 381 681 A | 1/1975 |
| GB | 1448533 | 9/1976 |
| JP | 54-5888 | 1/1979 |
| JP | 52-71015 | 10/1993 |
| JP | 07-155750 | 6/1995 |
| JP | 07-265865 | 10/1995 |
| JP | 09-253643 | 9/1997 |
| JP | 10-174970 * | 6/1998 |
| JP | P2000-126767 * | 5/2000 |
| JP | 2001-79358 | 3/2001 |
| JP | 2001-79553 | 3/2001 |
| JP | 2001-104960 | 4/2001 |
| JP | 2001-113137 | 4/2001 |
| JP | 2001-113279 | 4/2001 |
| JP | 2001-113280 | 4/2001 |
| JP | 2001-121152 | 5/2001 |
| JP | 2002-126744 | 5/2002 |
| JP | 2005007347 | 1/2005 |
| JP | 2005007348 | 1/2005 |
| RO | 114 874 B | 8/1999 |
| WO | WO 92/03202 | 3/1992 |
| WO | WO 92/11089 | 7/1992 |
| WO | WO 95/32052 | 11/1995 |
| WO | WO 95/32791 | 12/1995 |
| WO | WO 96/22162 | 7/1996 |
| WO | WO 97/25147 | 7/1997 |
| WO | WO 97/46491 | 12/1997 |
| WO | WO 97/46492 | 12/1997 |
| WO | WO 98/11987 | 3/1998 |
| WO | WO 98/17590 | 4/1998 |
| WO | WO 98/20972 | 5/1998 |
| WO | WO 98/58727 A1 | 12/1998 |
| WO | WO 99/39810 | 8/1999 |
| WO | WO 00/30749 | 6/2000 |
| WO | WO 00/64325 A2 | 11/2000 |
| WO | WO 00/75082 A1 | 12/2000 |

| | | |
|---|---|---|
| WO | WO 01/49397 A1 | 7/2001 |
| WO | WO 02/04357 A1 | 1/2002 |
| WO | WO 02/14224 A1 | 2/2002 |
| WO | WO 02/26629 A2 | 4/2002 |
| WO | WO 03/040042 A1 | 5/2003 |
| WO | WO 03/086590 A1 | 10/2003 |

OTHER PUBLICATIONS

U.S. Appl. No. 60/388,507, filed Jun. 12, 2002 by Beeman et al for the 6,773,588 patent.*

Yoram Oren et al., "Studies on polarity reversal with continuous deionization," *Desalination*, Elsevier Scientific Publishing Co., Amsterdam, NL, vol. 86, No. 2, Jun. 1, 1992, pp. 155-171.

ASTM, "Standard Practice for Calculation and Adjustment of the Langelier Saturation Index for Reverse Osmosis," Designation: D3739-94 (Reapproved 1998), pp. 1-4.

Dow Chemical, "Dowex Marathon A Ion Exchange Resin," published Dec. 1999, Product Literature reprinted from www.dow.com.

Dow Chemical, "Dowex Marathon A2 Ion Exchange Resin," published Nov. 1998, Product Literature reprinted from www.dow.com.

Dupont Nafion Products, Technical Information, "Safe Handling and Use," 1993, 4 pages.

FDA, "Guide to Inspections of High Purity Water Systems," printed from www.fda.gov. on Mar. 30, 2004, publication date unknown.

Glueckauf, "Electro-Deionisation Through a Packed Bed," *British Chemical Engineering*, Dec. 1959, pp. 646-651.

Hobro et al., "Recycling of Chromium from Metal Finishing Waste Waters Using Electrochemical Ion Exchange (EIX)," 1994, pp. 173-183, publication and date unknown.

Johnson et al., "Desalting by Means of Porous Carbon Electrodes," *Electrochemical Technology*, vol. 118, No. 3, Mar. 1971, pp. 510-517.

Kedem et al., "EDS—Sealed Cell Electrodialysis," *Desalination*, vol. 46, 1983, pp. 291-299.

Kedem et al., "Reduction of Polarization by Ion-Conduction Spacers: Theoretical Evaluation of a Model System," *Desalination*, vol. 27, 1978, pp. 143-156.

Korngold, "Electrodialysis Process Using Ion Exchange Resins Between Membranes," *Desalination*, vol. 16, 1975, pp. 225-233.

Purolite Technical Bulletin, Hypersol-Macronet™ Sorbent Resins, 1995.

R. Simons, "Strong Electric Field Effects on Proton Transfer Between Membrane-Bound Amines and Water," *Nature*, vol. 280, Aug. 30, 1979, pp. 824-826.

R. Simons, "Electric Field Effects on Proton Transfer Between Ionizable Groups and Water in Ion Exchange Membranes," *Electrochimica Acta*, vol. 29, No. 2, 1984, pp. 151-158.

R. Simons, "Water Splitting In Ion Exchange Membranes," Pergamon Press Ltd., 1983, 1984, pp. 275-282.

R. Simons, "The Origin and Elimination of Water Splitting in Ion Exchange Membranes During Water Demineralisation By Electrodialysis," *Desalination*, vol. 28, Jan. 29, 1979, pp. 41-42.

Walters et al., "Concentration of Radioactive Aqueous Wastes," *Industrial and Engineering Chemistry*, Jan. 1955, pp. 61-67.

Warshawsky et al., "Thermally Regenerable Polymerable Polymeric Crown Ethers, II Synthesis and Application in Electrodialysis," pp. 579-584, publication and date unknown.

International Search Report for International Application No. PCT/US 03/033818, mailed Mar. 29, 2004.

Chemical Processing, *Family of High Temperature RO Membrane Elements*, Product News, p. 1., Aug. 15, 2002.

Osmonics® Hot-Water Sanitizable RO Systems, Specifications, pp. 1-2. Copyright 2000 Osmonics, Inc., www.osmonics.com.

Peterson, R.J. et al., *Temperature-Resistant Elements For Reverse Osmosis Treatment of Hot Process Waters*, Published Dec. 1983, Filmtec Corporation, Minneapolis, Minnesota 55435. Prepared for the U.S. Department of Emergy, Under DOE Contract No. DE-FC07-82ID12423 (DOE/ID/12423-TI—DE84005190), pp. 1-69.

Reverse Osmosis Membrane Elements—131 Duratherm®, pp. 1-2, www.osmonics.com.

U.S.P. Requirements for Water for Injection, pp. 1752-1753, 1927-1929, Aug. 2002.

Weitnauer, Angella et al., Reverse Osmosis for WFI and PW, Published in: *Ultrapure Water*, Date published—Mar. 1, 1996, pp. 1-6, www.osmonics.com.

Wise, Brian, Chemical Processing, *Turning Up the Heat*, Hot Water Sanitation Membranes Tackle Microbes in RO Permeate Water, pp. 1-6, Aug. 2002.

Wise, Brian et al., *Hot Water Sanitization & RO: A Plain and Simple Introduction*, Presented at: Water Conditioning & Purification Magazine; Date Presented: Feb. 1, 2002. Osmonics®, pp. 1-6, www.osmonics.com.

Wood, Honathan et al., *The Use of Hot Water for Sanitization of RO Membranes in Ultrapure Water Systems*, U.S. Filter/Ionpure Inc., Lowell, MA, USA. Oct. 25, 1995. Presented at the 1997 Fifteenth Annual Membrane Technology/Separations Planning Conference, sponsored by Business Communications Co., Inc., Newton, MA, Oct. 29, 1997, pp. 1-10.

International Search Report, dated Mar. 7, 2005, PCT/US2004/037898.

* cited by examiner

PRODUCTION OF WATER FOR INJECTION USING REVERSE OSMOSIS

RELATED APPLICATIONS

This application is a continuation of U.S. application Ser. No. 10/278,714, filed Oct. 23, 2002, which is hereby incorporated by reference.

BACKGROUND

1. Field of Invention

This application relates to the production of United States Pharmacopeia (U.S.P.) Water for Injection (WFI) and, more specifically, to the production of Water for Injection using reverse osmosis.

2. Discussion of Related Art

Water for Injection (WFI) is purified water used in formulation of a product that may be administered parenterally to a patient. This highly purified pharmaceutical grade of water is subject to a number of requirements regarding purity and sterility. Under current U.S.P. regulations, WFI can be produced through either distillation or reverse osmosis (RO) treatment of a feed water that itself meets U.S.E.P.A. National Primary Drinking Water Regulations. While treatment by RO is allowed under the regulations, it is not typically used in practice due to a number of drawbacks, including the possibility of downstream microbial growth (despite periodic sanitization) and the possible leaching of organic components from the RO membrane and other synthetic materials that form the RO cartridge.

U.S.P. requirements for WFI include a conductivity of less than 1.3 $\mu$S/cm at 25° C. Total organic carbon (TOC) is required to be below a level of 500 ppb, measured as carbon, and bacterial endotoxins must not exceed more than 0.25 U.S.P. endotoxin unit (EU) per milliliter. Thus, not only should bacteria be excluded, but bacterial endotoxins should also be excluded or otherwise controlled.

As a result of these impracticalities and others, the production of WFI by RO has not been widely practiced.

SUMMARY

In one aspect of the invention, a method of producing Water for Injection is provided. The method includes the steps of providing feed water to a high pressure side of a reverse osmosis membrane, collecting the Water for Injection from a low pressure side of the membrane, and maintaining the membrane in a constantly self-sanitizing condition while producing the Water for Injection.

In another aspect of the invention, a system for producing Water for Injection is provided. The system includes a reverse osmosis unit including a reverse osmosis membrane, a heater upstream of the reverse osmosis membrane, and a high temperature storage vessel downstream of the membrane.

In another aspect of the invention, a method of facilitating the production of Water for Injection is provided. The method includes providing a reverse osmosis water purification system having means for maintaining a temperature of a reverse osmosis membrane at greater than 60° C. during production of Water for Injection.

In another aspect of the invention, a method for testing a membrane is provided. The method includes the steps of adding a known amount of a solute to a water sample to produce a test water, supplying the test water to a high pressure side of a membrane, detecting a solute concentration in a second water obtained from a low pressure side of the membrane, and determining the integrity of the membrane.

Other advantages, novel features, and objects of the invention will become apparent from the following detailed description of non-limiting embodiments of the invention when considered in conjunction with the accompanying drawings, which are schematic and which are not intended to be drawn to scale. In the FIGURES, each identical or nearly identical component that is illustrated in various FIGURES typically is represented by a single numeral. For purposes of clarity, not every component is labeled in every FIGURE, nor is every component of each embodiment of the invention shown where illustration is not necessary to allow those of ordinary skill in the art to understand the invention. In cases where the present specification and a document incorporated by reference include conflicting disclosure, the present specification shall control.

DETAILED DESCRIPTION

Figure 1:
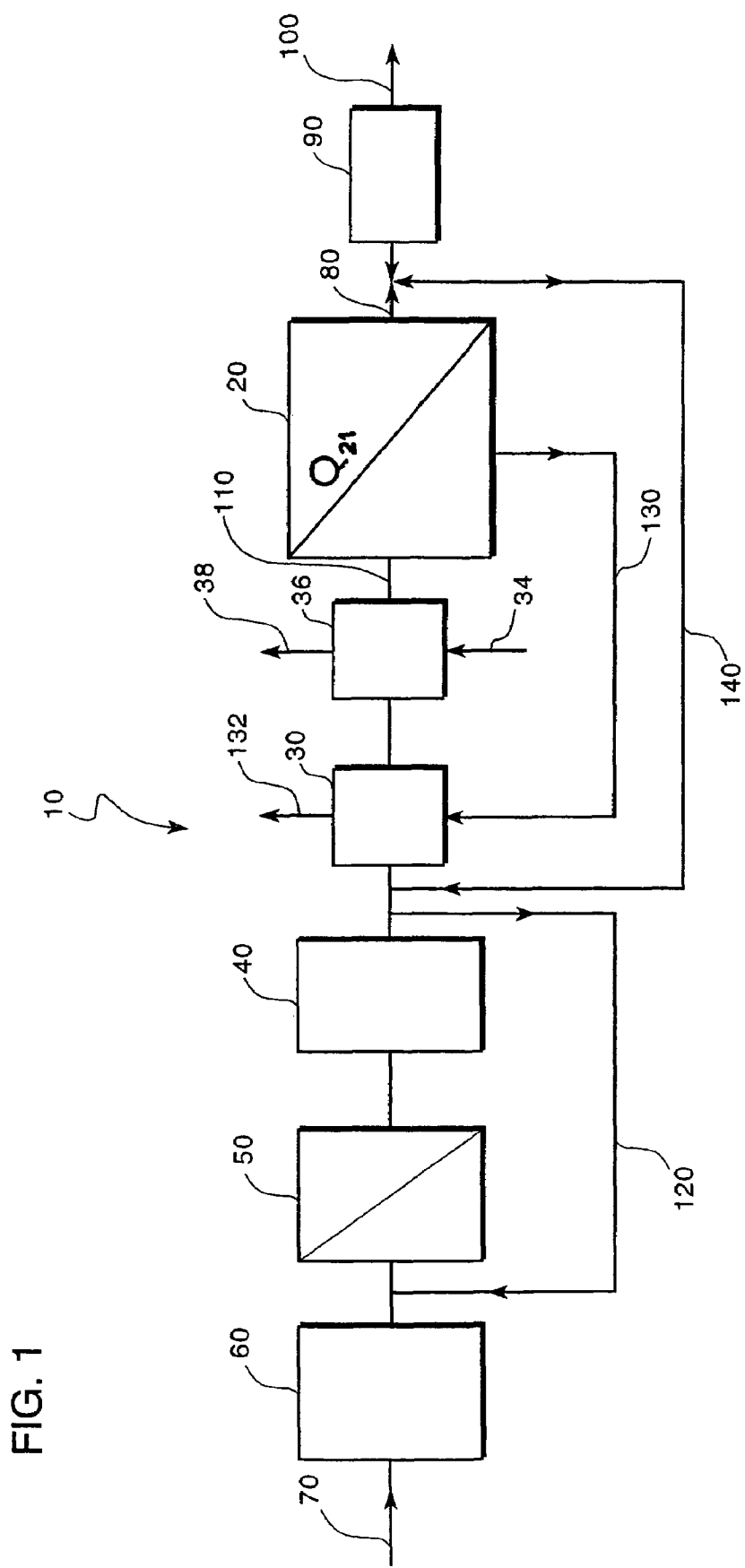
FIG. 1 is a schematic diagram showing a system of the invention.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein, is meant to encompass the items listed thereafter, and equivalents thereof, as well as additional items.

The invention provides a method for producing WFI using reverse osmosis. The RO membrane may be maintained in a constantly self-sanitizing condition. One way this condition may be achieved is by operating continuously at elevated temperatures.

Water for Injection (WFI) is water that meets the U.S.P. requirements (or foreign equivalent) for "Water for Injection." These requirements include bacterial endotoxins of not more than 0.25 U.S.P. EU per mL, total organic carbon (TOC) content of <500 parts per billion (ppb), and conductivity of 1.3 $\mu$S/cm. Water for Injection also includes compendial and non-compendial water classifications that meet the requirements of U.S.P. Water for Injection. Examples include water labeled or marketed as "Low Endotoxin U.S.P. Purified Water" and "WFI Quality Water."

Reverse osmosis (RO) is a process by which pressurized water passes through a semi-permeable membrane to remove a portion of the dissolved organic and inorganic compounds.

A "constantly self-sanitizing condition" describes an environment under which bacteria of concern do not reproduce and do not produce measurable levels of endotoxin. One method of maintaining a continuously self-sanitizing condition includes maintaining a reverse osmosis membrane at an elevated temperature of at least about 60° C.

Hot water sanitization (periodic sanitization) may be used to intermittently sanitize a reverse osmosis membrane. As is known to those skilled in the art, the term "hot water sanitizing" or "hot water sanitization" refers to periodic sanitation with hot water, and not to a continuous process. Hot water sanitization is not performed during the production of purified water. During a period of hot water sanitization, for example, for 30 or 60 minutes, purified water production ceases and the RO system is sanitized for subsequent use. During this process, the temperature of the system may be raised to, for example, 80° C., for a period of 30 to 90 minutes. After the specified time, the system is allowed to cool and can be placed back into production. As repeated heating and cooling may damage an RO membrane and/or its associated components as systems are heated and cooled, the rate of temperature increase or decrease may be controlled to minimize this damage to the membrane and its associated components.

When hot water sanitization procedures are practiced, trans-membrane pressures are typically maintained below about 40 psi during the sanitization phase. Temperatures in a range of 70-80° C. have been used, typically for periods of 30-60 minutes. Other periodic sanitization techniques, such as chemical sanitization, have also been practiced, but these techniques require the use of hazardous chemicals that may not be completely effective and that can be difficult to rinse out of the membrane after sanitization.

While hot water sanitization is useful in stopping bacterial growth and for temporarily reducing any build up of bacteria, e.g., biofilms, it does not eliminate the possibility of bacterial growth during water production at ambient temperature. In addition to the growth of microorganisms, the resultant production of microbial endotoxins may also be a concern. For example, bacteria growing on the upstream (high pressure) side of the RO membrane may pass through a defect in the membrane, colonizing the downstream side and may then produce levels of endotoxins that exceed U.S.P. requirements. Thus, reduction in microbial activity on the upstream side of the membrane may be as important as in the permeate stream itself.

There are a variety of reasons that continuous sanitization techniques have not been developed for systems for producing WFI. For example, at higher temperatures, RO membranes typically become less efficient and the passage of salts may become excessive, resulting in non-conforming water. Typically, the higher the temperature, the less efficient a membrane is at rejecting salts. High temperature operation may also lead to the leaching of organic materials from the membrane. This may result in high TOC levels and may be of specific concern in applications, such as the production of WFI, where low TOC levels are required. Other components of the system, such as the cartridge or housing, tubing, valves, gaskets and adhesives, may also contribute to TOC through high temperature leaching. Thus, for these reasons, and others, the operation of an RO membrane at a consistently high temperature for the production of WFI has not, until now, been practiced.

It has been found that some RO membranes can produce purified water suitable for WFI under constantly high temperature conditions. These membranes may provide for low carbon extraction and can produce water that passes U.S.P. requirements for WFI. These membranes may provide for a level of salt exclusion that can produce a product water meeting the required conductivity levels and that does not contain TOC at a concentration greater than that allowed by the U.S.P. regulations. The water may also meet the U.S.P. requirements for levels of endotoxin.

In one aspect, the present invention provides a method for providing WFI using an RO membrane. The RO membrane can be operated under constantly self-sanitizing conditions providing water that can consistently and reliably meet the U.S.P. requirement for WFI.

Some reverse osmosis membranes producing WFI at high temperatures may be durable at elevated temperatures and may exhibit properties of low TOC extraction and provide a level of salt exclusion resulting in conductivity levels adequate to meet U.S.P. requirements. Any membrane that can produce WFI while continuously withstanding temperatures of greater than or equal to 60° C. may be used. The membrane may possess good salt rejection properties at elevated temperatures, such as greater than 60° C. Preferably, the membrane does not contribute to TOC when operated in this temperature range. The membrane may be durable over this temperature range for extended periods of time while exhibiting good salt rejection qualities. The membranes may be operated at any pressure that results in an adequate flow of WFI from the membrane while providing an acceptable salt rejection level. As the quality of the feed water increases, the acceptable salt rejection level may be lowered, as less salt needs to be removed from the feed stream in order to meet the U.S.P. requirements.

In one embodiment, a membrane may be durable at greater than or equal to 65° C. for at least about 24 hours when producing WFI at a wide range of trans-membrane pressures. As WFI is most commonly stored at temperatures greater than 65° C. (ISPE Water and Steam Systems Guide) the RO membrane may be operated at a similar temperature. In this manner, the temperature of the water may be raised once, and then maintained. In one embodiment, the membrane may be made of a polyamid-type polymer. One class of membranes that may exhibit long term durability at temperatures of at least about 65° C. and may be used for producing WFI at continuously elevated temperatures is the polyamid thin film composite type. In one embodiment, the ESPA2-4038-46HT RO membrane (Hydranautics, Oceanside, Calif.) has been shown to provide acceptable results and can be operated for extended times at temperatures exceeding 90° C.

In one embodiment, an RO unit is operated at an elevated temperature. An elevated temperature is one greater than or equal to 60° C. In some embodiments other temperature ranges may be used. For example, a membrane may be kept self-sanitizing at a temperature of greater than 65° C., greater than 70° C., greater than 80° C. or greater than 90° C. If the system is pressurized, temperatures of 100° C., and higher, may also be used. Preferred temperature ranges may be chosen by the operator and may be based on, for example, membrane durability, salt rejection, and/or a self-sanitization temperature deemed adequate by the operator to suppress microbial growth for a specific system.

Other wetable components in the RO unit may also be subjected to these same temperatures. The water in the unit, and, as a result, the RO membrane contained therein, can be heated by any method or system capable of obtaining and maintaining the desired temperature levels. For example, a heat exchanger may be placed upstream of the RO unit in order to elevate the temperature of the water to a level required for continuous sanitization. Optionally, the water temperature may be raised to a level higher than that required to produce a constantly self-sanitizing condition. In this manner, even after some passive cooling, an adequate sanitization temperature can be maintained for wetable parts. The water may also be directly heated by the direct application of heat to a tank or conduit or the RO unit itself. For example, a resistance heating element may be used to heat a conduit providing feed water to the RO unit. Alternatively, temperature can be controlled by dividing the feed into two streams, one of which is heated and one of which is not, and then mixing the streams in an appropriate ratio to obtain a final desired temperature.

Regardless of the technique used for obtaining an increase in, or maintenance of, temperature, the heating system may be controlled by the use of a temperature-based feedback loop that may react to, for example, change in water temperature and/or a change in flow of the water through the system.

Temperature detectors 21, such as thermocouples, may be placed at one or more points in the system to monitor the temperature of the water or of the system in various locations. Signals from these detectors may be used to control the heating system and the signals may be recorded to verify, for example, that the RO unit has been kept in a constantly self-sanitizing state.

In another aspect, a reverse osmosis membrane cartridge is provided in which additional wetable components in the cartridge are maintained in a continuously self-sanitizing condition during production of purified water.

In one embodiment, materials in the RO membrane cartridge are formed from materials that meet U.S.P. Class VI toxicity requirements and do not provide a leachable source of contaminants, such as TOC. Furthermore, the membrane and cartridge may be capable of full and even heat distribution when hot water is used to heat the cartridge. The cartridge may have an absence of pockets that would remain below temperature and may be designed so that heat loss from any particular area of the cartridge is minimized in order to maintain all, or mostly all, of the wetable components at a temperature adequate to place the cartridge in a constantly self-sanitizing state. Some suitable configurations may include a "full-fit," a "loose-wrap," or a "brine seal" type construction, such designs being familiar to those skilled in the art.

A system used to produce WFI may include adhesives and connectors designed to limit levels of TOC and other potential contaminants, particularly in the presence of high temperature water. Furthermore, ancillary parts such as adhesives and connectors may be designed or chosen to withstand consistent temperatures of greater than 60° C. These parts may be employed in a system for producing WFI without significantly contributing to conductivity or TOC.

In one embodiment, a method is provided for the production of WFI without additional microbial control devices downstream of the RO membrane. As U.S.P. requires that the final purification step be RO or distillation, it may be preferred to package or store the WFI immediately after its production.

In another embodiment, a method provides for a continuous high temperature reverse osmosis procedure that may be preceded by one or more pre-treatment steps. Pre-treatment steps may include one or more techniques to provide water meeting U.S.P. requirements, or the equivalent, to an RO system. Pre-treatment may serve to treat or condition the water to an extent that after subsequent treatment via an RO membrane at an elevated temperature, the resulting permeate meets U.S.P. requirements for WFI. For example, if an RO membrane operating at a temperature of 80° C. rejects about 95% of the salt in the feedstream, the pre-treatment step, or steps, may be chosen to supply a feedstream that will result in water meeting the WFI requirements after removal of 95% of the salts contained therein. It is appreciated that margins of safety may be included to anticipate variations in system efficiency or water quality.

Pre-treatment steps may include, for example, disinfection, filtration, softening, anti-scalant injection, degasification, pH adjustment, deionization, chemical deionization, continuous electro-deionization, ultraviolet treatment, carbon bed filtration, reverse osmosis and others. Combinations of any of those methods may also be used. Filtration techniques may include microfiltration and ultrafiltration and multiple pre-treatment steps may be used in a single process or system. Pre-treatment steps may include recycle loops or direct flow systems. A heater, such as a heat exchanger, may be used upstream of the high temperature RO unit, and in one embodiment may be placed directly upstream of the high temperature RO unit. The salt content of the pre-treated water may be reduced to below a level necessary to avoid scaling or precipitation that may occur as a result of heating the water to a temperature of, for example, greater than 80° C. In some embodiments, to accommodate cooling that may occur between a heat exchanger and an RO module, the water may be pre-treated in preparation for being heated to, for example, greater than 90° C. The salt concentration may be reduced prior to heating the water.

Feed water conductivity may be at any level that can be reduced to, or maintained at, a level meeting the WFI requirements after the water has passed through the membrane. This may depend on a number of factors, for example, membrane efficiency, temperature, pressure, flow rate, and others. In some embodiments, feed water conductivity may be greater than 50 µS/cm while in other embodiments, it may be less than 50 µS/cm, less than 20 µS/cm, less than 10 µS/cm, or less than 1 µS/cm.

In another aspect, a system is provided. The system may include a continuous high temperature RO membrane and may include pre and/or post treatment devices or processes. For example, the system may include any of the pre-treatment devices provided above. The system may also include post-treatment devices or processes, such as, for example, packaging or chemical fortification, such as with a preservative. Production of WFI may also be followed by storage of the water, for example, at ambient temperature, high temperature, or low temperature. Post-treatment processes may result in the production of additional U.S.P. grade waters, such as Bacteriostatic Water for Injection (WFI containing an antimicrobial agent), Sterile Water for Inhalation (containing not more than 0.5 U.S.P. Endotoxin Unit per mL), Sterile Water for Injection (WFI packaged in single-dose glass or plastic containers) or Sterile Water for Irrigation (WFI labeled for irrigation only).

In one embodiment, WFI received from a high temperature RO device may be stored at an elevated temperature, for example, in a high temperature storage vessel. A high temperature storage vessel is a container that maintains any water contained therein at a temperature that is adequate to prevent microbial growth. For example, the water may be stored at greater than or equal to 65° C. This may serve to maintain the water in a self-sanitizing condition so that it may be classified, stored and used as WFI. In this manner, a high temperature RO system may supply water at a constant rate with a storage capability allowing for a supply of WFI that can accommodate periods of high and low demand.

In another embodiment, water from a high temperature RO system may be directly or indirectly packaged as WFI. The packaged WFI may then be distributed for use, for example, as a carrier for parenterally administered pharmaceuticals. The WFI may also be packaged and labeled as Sterile Water for Inhalation, Sterile Water for Injection or Sterile Water for Irrigation, according to U.S.P. regulations.

WFI made according to the invention may also be treated with an anti-microbial agent and packaged as Bacteriostatic Water for Injection.

In another aspect, a method for testing membrane integrity is provided. A membrane may be supplied with a feed stream containing a solute at a known concentration. The downstream (permeate) concentration of the solute may then be detected to indicate whether a defect exists in the membrane. The solute may be a material that can be efficiently removed by a properly operating membrane.

Membranes, such as reverse osmosis membranes, may fail at times, allowing the intrusion of undesirable microorganisms or other materials into the treated water. The failure may not be apparent to the operator and may be difficult to detect. A failure may be the result of a single breach large enough to allow the passage of microorganisms of concern or may be the result of a number of small defects. The breach may be of such a size that there is no easily detectable difference in flow and no discernable pressure drop during operation. Some tests known to those skilled in the art, such as the "forward flow test," may be used to determine if a breach of a specific magnitude exists but may not be sensitive enough to detect many of the defects of concern.

In one embodiment, a solution, such as a salt solution, may be used to challenge the integrity of a membrane. The test may be performed at an elevated temperature, for example, greater than or equal to 60° C. or greater than or equal 80° C., or may be completed at ambient, or even below ambient, temperatures. The membrane need not be removed from the pressure vessel and does not necessarily need to be cooled below the self-sanitization temperature. In this manner, the opportunity for bacterial growth may be precluded.

A properly performing membrane may be capable of removing a large portion of a solute, such as salt, from a feed stream. For example, 98 or 99% of the salt present may be removed by a typical RO system. However, if a membrane develops an integrity breach, a portion of the feed water may pass through the breach, and this portion may not be subjected to a significant decrease in salt content. This resulting high concentration stream may mix with lower concentration water on the downstream side of the membrane and may contribute to an overall increase in the salt concentration of the permeate. Such a contribution can be detected by a number of means, such as by a change in conductivity or by any other technique that can detect a solute concentration. A combination solute/analytical technique may be chosen that can provide a reliable indication of a small increase in solute concentration.

Smaller breaches, or defects, may be more readily detected when more efficient membranes are used. As membrane efficiency increases, the solute concentration in the permeate becomes lower, and any contribution made by the direct flow of test solution through a breach may constitute a greater percentage of the measured total solute concentration (e.g., conductivity) in the permeate. As a result, greater test sensitivity may be achieved by choosing a test solute that is more efficiently removed by the membrane being tested. For example, solutes that can be removed at 99.9% may be preferred to those that are removed at 99.5% and those that can be removed at 99.99% may be preferred to those that can be removed at 99.9%. In some embodiments, therefore, it may be preferred to use a test solute that includes a specific solute or class of solutes known to be efficiently removed by the membrane being tested. For example, a polyvalent salt such as magnesium sulfate, may be preferred as a challenge solute when polyvalent salts are most efficiently removed by the membrane.

Test solutes may also be chosen by the sensitivity with which they can be detected. For example, a solute that makes a significant contribution to conductivity (on a molar basis) when compared to other solutes may be preferred. Solute specific methods of analysis may also be used. In one embodiment, anions or cations for which sensitive measurement techniques, such as ion specific electrodes, are available, may be preferred because a slight change in concentration may be detected and precisely quantified. This detection and quantification may allow the test personnel to more accurately determine the severity of any defect.

Therefore, in a preferred embodiment, a test solute may be chosen that can be efficiently removed by the membrane being tested, can be detected in small quantities in solution, and/or is not harmful in the intended use of the purified water.

For example, an RO membrane may be tested at an elevated temperature, for example, at 80° C. A solute may be chosen that is subject to a high exclusion rate when applied to the membrane being tested. For example, the solute may be a salt that may be excluded at a rate of greater than 99.5% when the membrane is performing properly. The salt may be supplied to the feed stream to form a feed stream having a concentration adequate to result in a detectable downstream response in the presence of a defect. In some embodiments, solute concentration may range between 100 and 10,000 ppm. In one embodiment, the solute concentration is between 1,000 and 2,000 ppm. After the high solute feed stream is fed to the membrane, the resulting downstream concentration may then be measured, for example, by detecting the conductivity of the permeate. This may be done after providing adequate time for the permeate to mix and equilibrate, thus providing a homogeneous solution. If the permeate stream shows a solute concentration above a pre-determined limit, then the operator may be alerted that a defect could exist somewhere in the system. If the results are below the pre-determined limit, then the membrane, or system, may be assumed to be free of defects of concern. In this case, a decision may be made to keep the membrane in service. As the test may be performed on a system using multiple RO cartridges, an expected concentration may be most easily calculated by computer projection. If a test shows that results are out of specification for the system, further tests may then be performed to determined which specific membrane or cartridge may be at fault.

FIG. 1 illustrates an embodiment of the invention that may include a continuous high temperature reverse osmosis device, pre-treatment options, one or more heat exchangers, and post-treatment options. WFI production system 10 includes a reverse osmosis unit 20 that may be operated at an elevated temperature, for example, greater than 60° C. RO unit 20 includes an RO membrane that may not contribute to TOC content at elevated temperatures, can remove salt to a level to meet WFI requirements and may be durable enough to operate at an elevated temperature for an extended time without a significant loss in efficiency. The membrane may be a polyamid thin film composite type membrane. The RO unit may operate continuously for more than about 150 hours with less than a 1% drop in the salt rejection rate.

The RO unit may be operated at an elevated temperature while operating over a broad pressure range. Any transmembrane pressure that provides adequate flow may be used. Preferred pressures may be chosen based on, for example, the properties of the membrane, the feed water quality and the desired flow rate. For example, pressures of greater than 20 psig, greater than 40 psig or greater than 60 psig may provide adequate flow with good salt rejection. In some cases, pressures of several hundred psig, or more, may be used. Reverse osmosis unit 20 may include a pump for providing high pressure water to the membrane.

Feed water enters RO unit 20 by way of conduit 110. Prior to passing through conduit 110, the feed water may be pre-treated and/or heated. Heat exchanger 36 can be used to raise the temperature of the feed water to a level adequate to maintain a constantly self-sanitizing condition in the RO unit. It is also appreciated that any heat source may be used to keep RO unit 20 at an adequate temperature. RO unit 20 may be insulated to minimize heat loss and to help provide heat to all wetable components of the unit. RO unit 20 may include one or more thermocouples that may be in communication with a controller. The thermocouples may be placed in any location on or in the unit, including areas that may be susceptible to cooling.

In one embodiment, the permeate may be recycled back into the system. This may result in the re-use of purified water and heat that would otherwise have been lost through the discharge of heated, purified water. The permeate may be directed by valve 150 to conduit 140 that will re-introduce the water upstream of pre-heater 30 and heat exchanger 36. Conduit 140 may be insulated to reduce heat loss and/or may be heated to maintain a continuously self-sanitizing condition. In this manner, RO unit 20 may be constantly operated, regardless of demand for WFI, and therefore kept at a sufficiently high temperature to maintain a constantly self-sanitizing condition. For example, if demand for WFI at outlet 100 has ceased, the flow of hot water through RO unit 20 need not stop, which could, in the absence of a recycling loop, or similar, lead to a cooling of RO unit 20 and possible deviation from a constantly self-sanitizing condition. A flow of hot water to the RO membrane can be used to maintain a constantly self-sanitizing condition even when downstream demand is reduced. The flow rate may be reduced to below that of normal operative rates.

Heat exchanger 36 can be heated by a heating medium passing through conduit 34 and out of the heat exchanger via conduit 38. Pre-heater 30 can be optionally heated by hot concentrate fluid from RO unit 20 via conduit 130, which may be insulated or heated, for example. This can help to recover heat (but typically not water) from the concentrate and serve to reduce the heating load on heat exchanger 36. Concentrate fluid may be discharged from conduit 132 after heat has been removed from it.

Pre-treatment devices 40, 50 and 60 may be fed at inlet 70 and may include one or more pre-treatment devices to prepare the water as a feedstream for WFI production via a constantly high temperature RO process. The combination of pre-treatment steps may be chosen to provide conduit 110 with water that will result in a permeate (at outlet 80 or outlet 100) meeting the requirements for WFI. Individually, these pre-treatment devices and processes can be selected from those known to one skilled in the art. For example, device 60 may be a softener, device 40 may be an electrodeionization device and device 50 may be a second RO device. In addition to these, pre-treatment stages may also include filtration, such as carbon filtration, and may include additional treatments such as pH adjustment. These pre-treatment devices or processes may be arranged in any desired manner to most effectively treat the feed water. Some or all pre-treatment stages may include a recycling loop as is illustrated by conduit 120.

Post-treatment processes and devices, such as storage vessel 90, may be included with the system. Post-treatment devices and processes may include storage vessels, packaging equipment, quality monitoring equipment and/or apparatus for adding materials such as preservatives to the water. For example, storage vessel 90 may be constructed to maintain the WFI permeate received from conduit 80 at an elevated temperature, for example, greater than or equal to 65° C. Packaging equipment may include a filling apparatus to be used to fill vials or bottles with water labeled as "WFI."

System 10 may include quality monitoring devices at any point. For example, conductivity, TOC and temperature may be monitored at inlet conduit 70, at any pre-treatment stage, at heat exchanger 36, at feedstream conduit 110, at continuous high temperature RO unit 20 or at post-treatment stage 90. Any or all of the quality monitoring devices used may be in communication with a controller, such as a computer, for aiding in monitoring, adjusting and controlling the system. For example, an increase in flow or a decrease in temperature may trigger an increase in heat provided by heat exchanger 36. Or, in another embodiment, an increase in conductivity might trigger an increase in voltage in an upstream electrodeionization device or might trigger a decrease in flow. Other controls and feedback loops will become apparent to one skilled in the art upon implementation of the system.

EXAMPLES

Example 1

In order to determine if WFI can be produced efficiently at consistently elevated temperatures, exclusion efficiency and permeate rates were measured for a polyamid thin film composite membrane at a temperature of 80° C. The membrane (ESPA2-4038-46HT from Hydranautics) was provided in a full-fit configuration with a total area of 65 square feet. Feed stream quality and pressure was maintained as indicated in Table 1. The percentage of salt passage/rejection was determined by measuring the conductivity of the permeate and the reject streams.

Table 1 provides results for salt rejection on feed waters containing 2000 ppm salt (measured as conductivity) and for a water having a conductivity of 10 μS/cm. Temperature and feedstream pressure are also provided. Higher temperatures may result in increased flow rates through a membrane. When the temperature was raised from 25 to 80° C., the trans-membrane pressure was reduced from 200 psig to 63 psig in order to maintain a flow rate of about 3.3 L/m.

TABLE 1

| Flow, lpm | T ° C. | PSIG | Feed | % Salt Rejection | % Salt Passage |
|---|---|---|---|---|---|
| 3.3 | 25 | 200 | 2000 ppm | 98.8-99.1 | 0.9-1.2 |
| 3.3 | 80 | 63 | 2000 ppm | 97.5 | 2.5 |
| 4.4 | 80 | 63 | 10 μS/cm | 85.0-88.0 | 12-15 |

The results show that salt rejection decreased from a range of 98.8-99.1% to a level of 97.5%. When fed at the same trans-membrane stream pressure as the 80° C., 2000 ppm sample, the flow rate of the 10 μS/cm water sample increased to 4.4 L/m. The salt rejection rate for this sample decreased to about 85.0-88.0%. These results, while showing a decrease in salt exclusion efficiency at the higher temperatures, indicate that salt exclusion was better than had been anticipated. Furthermore, the results indicate that WFI can be successfully produced at these continuously high temperatures, particularly when the feed stream is pre-treated to remove at least a portion of any dissolved salts. Desirable flow rates may also be maintained at significantly lower trans-membrane pressures (63 vs. 200 psig) when the membrane is operated at a higher temperature. This lower pressure operation may provide for a system resulting in less wear on the membrane and associated parts, as well as a reduction in pressure pump requirements when compared to a low temperature system at an equivalent flow rate.

Example 2

Additional tests were performed on the same membrane as in Example 1 to determine the effect of continuous high temperature operation of the polyamid thin film composite membrane regarding contribution or removal of TOC. Table 2 provides results from a series of tests that were run using feedstream waters of varying TOC content. The system was operated at a temperature of 80° C. and at a trans-membrane stream pressure of 63 psig. TOC was measured in the feed stream, the permeate and the reject using an ANATEL® A-100 Organic Analyzer (Loveland, Colo.).

TABLE 2

| Sample # | Feed TOC, ppb as C | Product TOC, ppb as C | % Rejection of TOC |
|---|---|---|---|
| 1 | 53.4 | 42.1 | 21.1 |
| 2 | 131.5 | 31.5 | 76.0 |
| 3 | 57.7 | 32.7 | 43.3 |
| 4 | 60.5 | 29.8 | 50.7 |
| 5 | 46.3 | 29.5 | 36.3 |
| 6 | 72.7 | 58.4 | 19.7 |
| 7 | 78.7 | 30.7 | 61.0 |

Feed stream TOC content ranged from 53.4 to 131.5 ppb, as carbon. Product (permeate) TOC content ranged from 29.5 to 58.4 ppb. Percent rejection of TOC ranged from 19.7% to 76.0%, indicating that TOC was removed from each sample. In some cases, TOC was rejected at a net rate greater than 60 or 70%. These results indicate that, rather than contributing to TOC, the membrane removes TOC from the water when operated at an elevated temperature, such as, at about 80° C. This reduces concerns about increased TOC levels due to high temperature leaching of organic materials from the membrane.

Example 3

An additional testing procedure was run to determine if the membrane of Example 1 could adequately reject endotoxins at an elevated temperature. Except where Otherwise indicated, the test was run as in Example 1. The membrane was challenged with feed water that had been spiked to levels of 800 and 62.5 EU/mL. The membrane was maintained at a self-sanitizing temperature of 80° C., the flow rate was 4.0 or 4.2 L/min, as shown below, and the average pressure on the RO element was 69.5 psig for Both test. Results are provided in Table 3.

TABLE 3

| Sample | Endotoxin level in feed (EU/mL) | Membrane Temperature | Feed pressure | Flow rate (L/min) | Endotoxin level in permeate |
|---|---|---|---|---|---|
| 1 | 800 | 80° C. | 69.5 psig | 4.0 | 0.03 EU/mL |
| 2 | 62.5 | 80° C. | 69.5 psig | 4.2 | <0.03 EU/mL |

The results indicate that at a temperature of 80° C., the membrane provides excellent rejection of endotoxins at levels up to and including 800 EU/mL. Levels for both permeates were well below the 0.25 EU/mL level, as required by the U.S.P. Thus, with this RO membrane system, an operator can be assured that endotoxin levels can be met while operating in a continuous self-sanitizing state.

Example 4

In order to determine the long term effects of high temperature operation on membrane efficiency, the membrane of Examples 1, 2 and 3 was continuously operated at a temperature of 80° C. and was periodically challenged with a salt solution (sodium chloride). Consistent salt rejection would indicate consistent rejection of bacteria and related pyrogens (endotoxins), as any integrity failure that would allow increased passage of bacteria or pyrogens would also be reflected in an increase in salt passage. The trans-membrane stream pressure was maintained at about 63 psig. The resulting salt Concentration in the permeate was measured and recorded.

TABLE 4

| Exposure Hours | Permeate lpm | Feed µS/cm | Product µS/cm | % Rejection |
|---|---|---|---|---|
| 0 | 5.8 | 3072 | 28.1 | 99.1 |
| 60 | 3.275 | 2930 | 33.2 | 98.9 |
| 158 | | 2900 | 35.5 | 98.8 |
| 317 | 3.55 | 3040 | 34.0 | 98.9 |
| 452 | 3.57 | 3050 | 36.5 | 98.8 |
| 526 | 3.65 | 3000 | 39.4 | 98.7 |
| 649 | 3.65 | 2960 | 38.4 | 98.7 |
| 816 | 3.725 | 2900 | 38.1 | 98.7 |

The results, as shown in Table 4, indicate that after high temperature continuous operation for 60, 158, or even 816 hours, the salt rejection rate was substantially the same (<1% decrease) as when the membrane was put into high temperature operation. Significantly, the minor decrease in rejection efficiency plateaued after about 60 hours of continuous high temperature use, indicating that the system could be used for significantly longer times than shown in this test. Thus, the membrane can be used at a continuous high temperature for long term, reliable production of WFI without allowing increased passage of pyrogens or bacteria.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A system for producing Water for Injection comprising:
a reverse osmosis unit comprising a water inlet, a water outlet, and a reverse osmosis membrane;
a temperature sensor positioned in the reverse osmosis unit;
a water heat exchanger positioned upstream of and fluidly connected to the reverse osmosis membrane;
a water pre-heater positioned upstream of and fluidly connected to the water heat exchanger and fluidly connected to a concentrate outlet of the reverse osmosis unit;

a controller responsive to a signal from the temperature sensor to provide a control signal to the water heat exchanger to maintain a water temperature at greater than or equal to 60 C. during water purification; and a storage vessel downstream of and fluidly connected to the reverse osmosis unit wherein the storage vessel maintains Water for Injection at an elevated temperature.

2. The system of claim 1, wherein the reverse osmosis membrane is made of a material capable of withstanding a temperature greater than or equal to 60° C.

3. The system of claim 2, further comprising means for continuously providing a trans-membrane stream at a pressure of greater than about 40 psig.

4. The system of claim 1, wherein the reverse osmosis membrane is made of a material capable of withstanding a temperature greater than or equal to 80° C.

5. The system of claim 1, wherein the storage vessel is constructed and arranged to maintain a temperature greater than or equal to 65° C.

6. The system of claim 1, further comprising a recycle loop providing fluid communication between a downstream side of the reverse osmosis membrane and the water heat exchanger.

7. The system of claim 1, further comprising a pretreatment device upstream of and fluidly connected to the water heat exchanger.

* * * * *